United States Patent
Schneeberger et al.

(10) Patent No.: US 12,290,606 B2
(45) Date of Patent: May 6, 2025

(54) METHOD FOR PRODUCING A DRUG DELIVERY SYSTEM

(71) Applicants: Laxxon Medical AG, Stetten (CH); Exentis Knowledge GmbH, Stetten (CH)

(72) Inventors: Achim Schneeberger, Vienna (AT); Klaus Kühne, Berlin (DE); Helmut Kerschbaumer, Zürich (CH); Srdan Vasic, Horgen (CH)

(73) Assignees: Laxxon Medical AG, Stetten (CH); Exentis Knowledge GmbH, Stetten (CH)

( * ) Notice: Subject to any disclaimer, the term of this patent is extended or adjusted under 35 U.S.C. 154(b) by 29 days.

(21) Appl. No.: 17/819,940

(22) Filed: Aug. 15, 2022

(65) Prior Publication Data
US 2023/0078273 A1    Mar. 16, 2023

Related U.S. Application Data

(62) Division of application No. 16/958,768, filed as application No. PCT/EP2017/084828 on Dec. 29, 2017, now Pat. No. 11,484,504.

(51) Int. Cl.
*A61K 9/20* (2006.01)
*A61K 9/70* (2006.01)
*A61P 31/00* (2006.01)
*B41M 1/18* (2006.01)
*A61K 45/06* (2006.01)

(52) U.S. Cl.
CPC .......... *A61K 9/2095* (2013.01); *A61K 9/2077* (2013.01); *A61K 9/7092* (2013.01); *A61K 45/06* (2013.01)

(58) Field of Classification Search
CPC .. A61K 9/2095; A61K 9/2077; A61K 9/7092; A61K 45/06; A61J 3/02; A61J 3/06; A61J 3/07; A61J 3/007; B41M 1/12; B41M 1/18; B41M 1/26; B41M 3/00; B41M 7/00; B41M 99/00; B41P 2200/40; B41P 2215/50
See application file for complete search history.

(56) References Cited

U.S. PATENT DOCUMENTS

2009/0041824 A1*  2/2009  Zugates .................. A61L 27/54
                                                    514/772.3

FOREIGN PATENT DOCUMENTS

| AU | 777621 B2 | 10/2004 |
| AU | 2005230752 B2 | 8/2010 |
| CN | 1377258 A | 10/2002 |
| CN | 101953777 A | 1/2011 |

(Continued)

OTHER PUBLICATIONS

Kumar, V. (Phytotherapy Research 2006;20:1023-1035). (Year: 2006).*

(Continued)

*Primary Examiner* — Ernst V Arnold
(74) *Attorney, Agent, or Firm* — Renner, Otto, Boisselle & Sklar, LLP

(57) ABSTRACT

The present invention relates to a method for producing a drug delivery system. The method comprises the steps of screen-printing a base paste, and curing the base paste. Furthermore, the method comprises the steps of screen-printing a first paste separate to the base paste, and curing the first paste.

33 Claims, 8 Drawing Sheets

(56) References Cited

FOREIGN PATENT DOCUMENTS

Figure 1A:
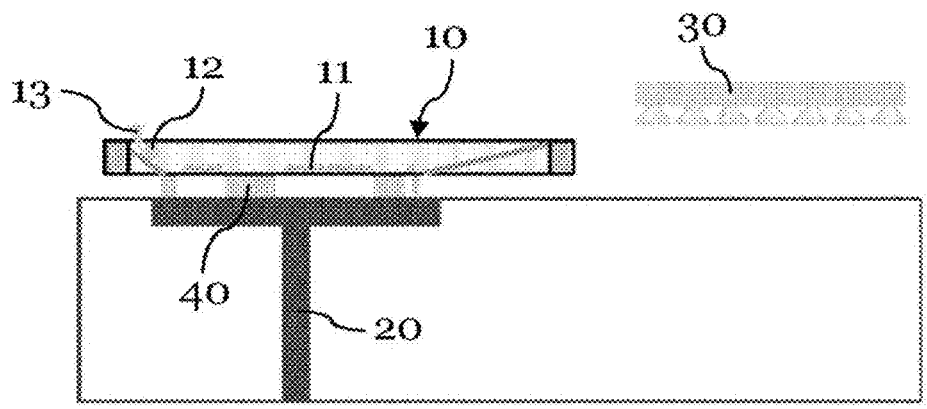

| EP | 0169364 A1 | 1/1986 |
| JP | 2002331640 A | 11/2002 |
| WO | 03/037607 A1 | 5/2003 |
| WO | 03/041690 A2 | 5/2003 |
| WO | 2009/020607 A2 | 2/2009 |

OTHER PUBLICATIONS

Gyllenhaal et al. (Sleep Medicine Reviews 2000;4(3):229-251). (Year: 2000).*
Dellemijn et al. (Journal of Pain and Symptom Management 1998; 16(4):220-229). (Year: 1998).*
U.S. Appl. No. 16/958,768, filed Jun. 29, 2020.
International Search Report and Written Opinion for corresponding International Patent Application No. PCT/EP2017/084828 dated Apr. 26, 2018.
International Preliminary Report on Patentability for corresponding International Patent Application No. PCT/EP2017/084828 dated Apr. 9, 2020.
Wenzel et al. (Hypertension 1998;32: 1022-1027). I et al. (Hypertension 1998;32: 1022-1027). (Year: 1998).
Second Japanese Office Action issued Nov. 24, 2021, for corresponding Japanese Application No. 2020-555295.
Original and English Translation of the First Chinese Office Action issued for corresponding Chinese Application No. 201780098307.1, dated Feb. 23, 2022.
Kolakovic et al. (Expert Opinion on Drug Delivery. 2013; 10(12): 1711-1723) (Year: 2013).
Yu et al. (Journal of Pharmaceutical Sciences 2008;97(9):3666-3690) (Year: 2008).

* cited by examiner

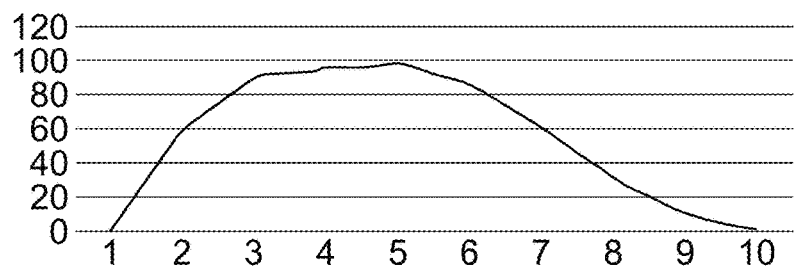 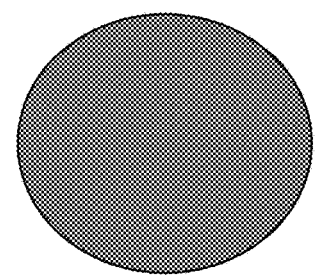
Fig. 6A
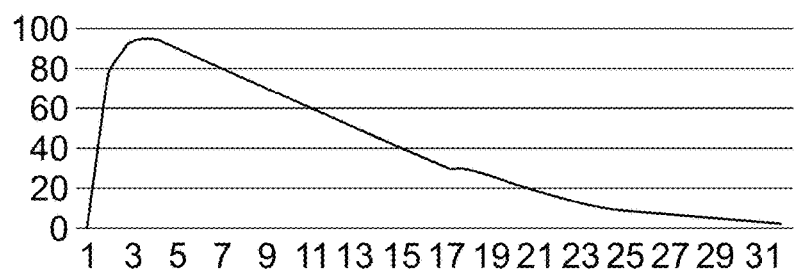 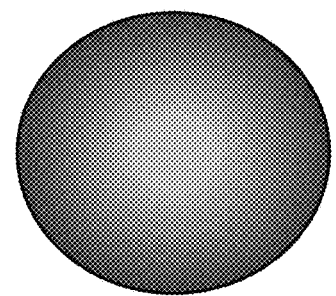
Fig. 6B
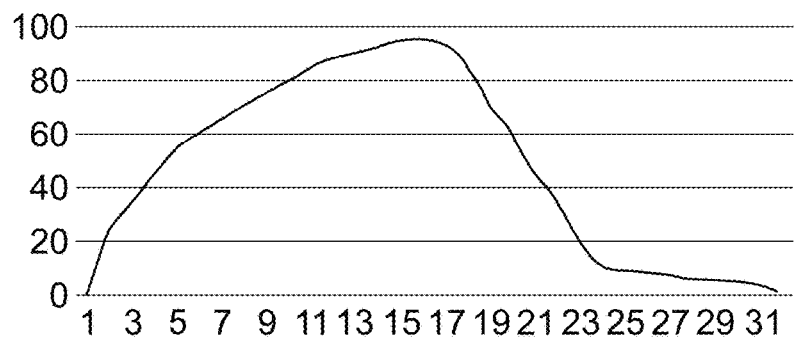 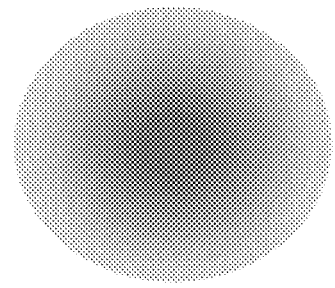
Fig. 6C

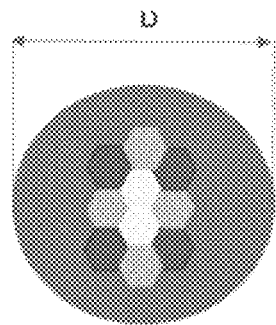
Fig. 7A
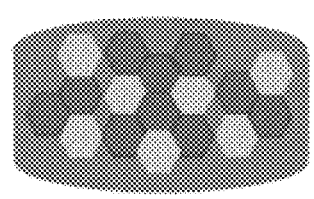
Fig. 7B
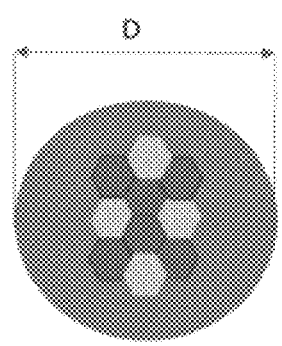
Fig. 7C
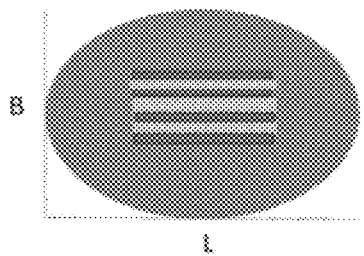
Fig. 7D
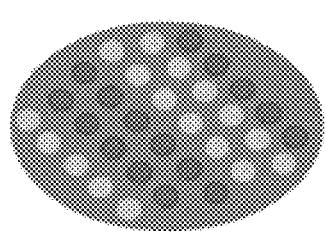
Fig. 7E
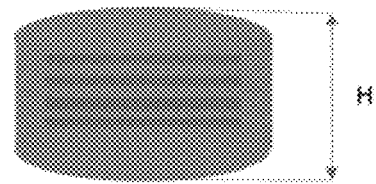
Fig. 7F
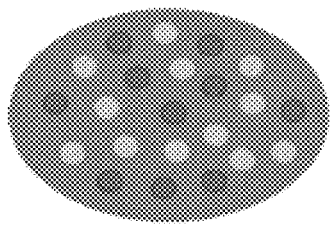
Fig. 7G
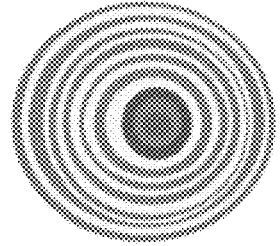
Fig. 7H
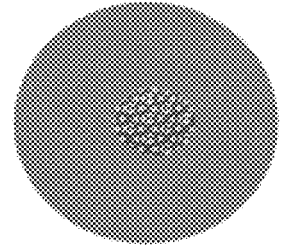
Fig. 7I
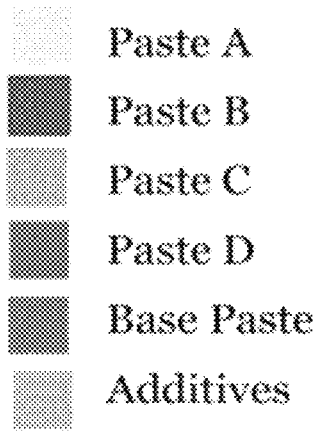
Paste A
Paste B
Paste C
Paste D
Base Paste
Additives

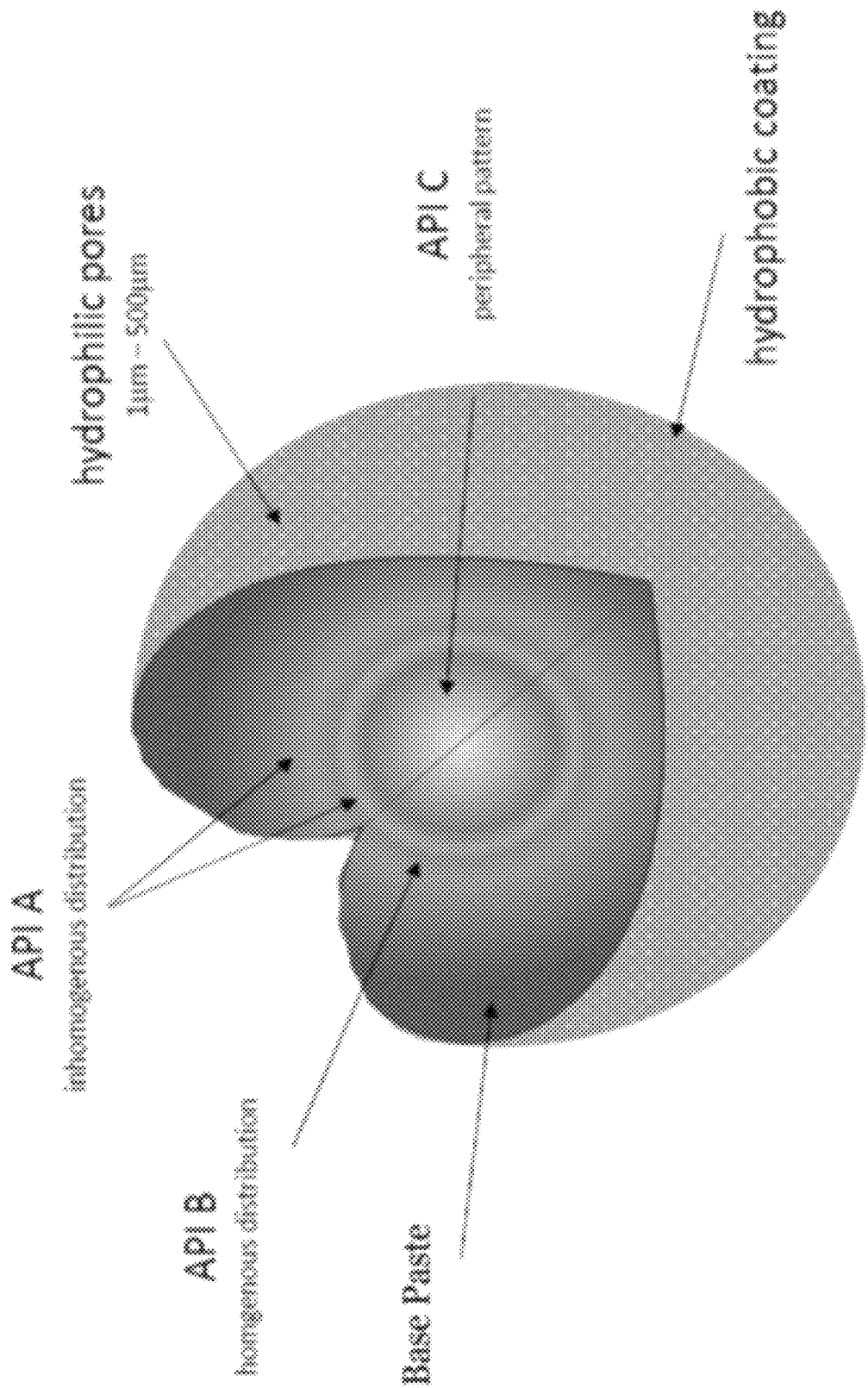

METHOD FOR PRODUCING A DRUG DELIVERY SYSTEM

1. RELATED APPLICATION DATA

This application is a division of U.S. patent application Ser. No. 16/958,768 filed Jun. 29, 2020, which is a national phase of International Application No. PCT/EP2017/084828 filed Dec. 29, 2017, and published in English under International Publication No. WO 2019/129361 A1 on Jul. 4, 2019, all of which are incorporated herein by reference.

2. FIELD OF THE INVENTION

The present invention relates to a method for producing a drug delivery system, the drug delivery system preferably being for a controlled, further preferred systemic administration of one or more active pharmaceutical ingredients to a body. Furthermore, the invention relates to a system for producing a drug delivery system.

3. TECHNICAL BACKGROUND

A drug, or a pharmaceutical drug, is commonly used for diagnosing, curing, treating or preventing diseases. An active pharmaceutical ingredient (API) may be the part of any drug that produces its effects. Some drugs may have multiple APIs to treat different symptoms or act in different ways. Thus, one or more APIs may be delivered by a drug. The delivery of drugs, or drug delivery, may refer to the transportation of a pharmaceutical compound into the body of a patient as needed to safely achieve its desired (therapeutic) effect. The delivery or administration of a drug into the body of a patient may be performed in various ways. The routes of administration include, among others, the intravenous (into the blood compartment through the puncture of a vein) and oral route (through the mouth of the patient, e.g. to enter via the oral mucosa or pass on into the gastrointestinal tract to reach the blood compartment via the gastric or intestinal mucosa). Drugs can further be administered by inhalation, by injection into tissues (e.g., subcutaneous, intramuscular) or by topical application (e.g., creams for use on the skin). Drugs can be provided in different dosage forms. The dosage forms may comprise, among others, pills, tablets, capsules, solutions, dispersions, emulsions, implants.

A tablet may be a pharmaceutical dosage form. A tablet may be a solid unit dosage form of a pharmaceutical drug comprising an API, with or without suitable excipients. Tablets may be produced either by molding or by compression. Upon manufacturing of a tablet, the main guideline is commonly to ensure that the appropriate amount of active pharmaceutical ingredient(s) is in each tablet. Therefore, all ingredients should be well mixed. Thereby, a homogeneous mixture of the ingredients is obtained. A particular amount of the mixture may then be compressed in order to obtain a tablet. Thus, the API is typically homogeneously distributed throughout the tablet, or parts of it.

Upon application of a tablet, for example upon oral administration, the tablet may dissolve and thereby the API may be released. It then passes the intestinal mucous membrane to reach the blood compartment and finally the tissue of action. With the commonly produced drug delivery systems, the concentration of the API within the blood compartment is typically such that, for a particular period of time only, it is above the efficacy threshold of the given API. During this period, the release of the API out of the drug delivery system into the gastrointestinal tract is however typically much higher than actually required, whereby the excess amount of the API may (i) not pass the membrane in sufficient amounts and be picked up by the body and, thus, may be excreted of (ii) may reach the blood compartment/the tissue to result in toxic effects.

According to the respective background of the drug application, or the particular therapeutic program, it may be desirable to have a particular release profile of the API. It may, for example, be desirable to release the API at the constant rate over a prolonged period of time. In other scenarios, it may be desirable to provide for a particularly slow release of an API to a body, with a release rate slightly above the efficacy threshold of the API, wherein the rate of release may be approximately independent of time. In further scenarios, it may be desirable to release the API at particular intervals, for example intermittently over time. In further scenarios, it may be desirable to release several APIs one after the other, or simultaneously at individual release rates, with API-specific release profiles.

Release of APIs out of common tablets, which are characterized by a homogeneous distribution of the APIs due to the requirements and limits of the conventional manufacturing technologies, is mainly driven by the size of the disintegrating tablet, in particular, the surface that is exposed to the surrounding fluid. As such it is predefined by the form and size of the tablet and fixed, with for example a high release at the beginning and lowering over time. The resulting blood/tissue concentrations of the API may thereby well exceed the respective efficacy threshold, in order to obtain a desired period of concentration above said threshold.

Such a release profile is particularly disadvantageous for APIs with a narrow therapeutic window (that is little difference between therapeutic and toxic dose). APIs with a narrow therapeutic index (NTI) include aminoglycosides, ciclosporin, carbamazepine, digoxin, digitoxin, flecainide, lithium, phenytoin, phenobarbital, rifampicin, theophylline, warfarin.

Reference U.S. Pat. No. 3,854,480 describes a drug delivery system for releasing an active pharmaceutical ingredient at a controlled rate for a prolonged period of time. The drug delivery system thereby comprises a solid inner matrix material having solid particles of the drug distributed therethrough, and an outer polymeric membrane, which is permeable and insoluble in body fluids and which surrounds the inner matrix. The outer polymeric membrane thereby continuously meters the flow of drug from the inner matrix material to the exterior of the system at a controlled and constant rate over a prolonged period of time. However, the drug delivery system according to U.S. Pat. No. 3,854,480 does not allow for more elaborate release profiles. Further, the administration of an insoluble polymeric membrane to the body of a patient may be disadvantageous.

Reference U.S. Pat. No. 5,674,530 A relates to a drug delivery system, wherein a first water permeable capsule half is filled with a drug and an osmotic agent. Reference US 2010/0068271 A1 relates to osmotic delivery systems employed in tablets, being divisible into two useable half-strength tablets. The release by means of osmotic effects is dependent, among others, on the environment of the drug delivery system in the patient, making a precise drug release at a desired target challenging. Thus, it is difficult to achieve a controlled and precise drug release with such systems. Furthermore, such systems do not allow for more elaborate release profiles.

Reference WO 1993/007861 A1 relates to drug delivery systems involving microcapsules or microspheres. Thereby multi-phase microspheres are described to include a molecular compound contained within a fixed oil within a polymeric matrix. The molecular compound may first have to traverse a water-oil barrier, and the polymer barrier of the polymer matrix, before it can diffuse out of the microsphere. Thereby, a constant and fixed rate of delivery of a molecular compound can provided without sacrificing high drug loading efficiency in the microsphere. However, this prior art system does not allow for more elaborate release profiles.

Reference WO 1999/008662 A1 relates to a drug delivery system suitable for oral administration that facilitates a two-step release of an active agent. A drug delivery system disclosed therein comprises a first drug compartment, a first polymer compartment substantially enveloping the first drug compartment, a second drug compartment enveloping the first polymer compartment, and a second polymer compartment enveloping the second drug compartment. The second polymer compartment, which may be of one or more water insoluble polymers, controls the release of an active agent from the second drug compartment. However, this prior art system does not allow for more elaborate release profiles.

The present invention aims at overcoming the disadvantages outlined above. Thus, one problem underlying the present invention is to provide a method for producing a more efficient drug delivery system which can advantageously provide for a controlled administration of one or more active pharmaceutical ingredients to a body, with an application-tailored, therapy-tailored and/or API-specific release profile. A further object of the present invention is to provide a method for producing a drug delivery system which allows for a controlled administration of several APIs to a body, such that the APIs are released relative to each other in a defined manner, preferably with desired API-specific release profiles. A general object of the invention can be formulated as to provide an improved technique for producing a drug delivery system, which allows for producing advanced drug delivery systems with high quality and in great quantities. The advanced drug delivery system may thereby optimize pharmacokinetics and pharmacodynamics.

These and other objects, which are apparent for the person skilled in the art from the following description, are solved by a method for producing a drug delivery system, a drug delivery system, and by systems for producing a drug delivery system.

4. SUMMARY OF THE INVENTION

The present invention relates to a method for producing a drug delivery system. Said drug delivery system may allow for transporting an active pharmaceutical ingredient (API) in the body of the patient as needed to safely achieve its desired therapeutic effect. The drug delivery system may thereby include an API, or several APIs, or other ingredients such as vitamins and minerals. The drug delivery system may be a bioerodible drug delivery system. Thus, the drug delivery system may erode upon application thereof to a body of a patient, and may, for example, dissolve upon application, e.g. in the mouth of the patient. The drug delivery system produced according to the present invention is particularly suited for a controlled administration of one or more APIs to a body. The body may be the body of a patient, which may be a human or an animal. Further in particular, the drug delivery system produced according to the present invention may be used for oral administration of one or more APIs to a body, whereby the drug delivery system may dissolve in the mouth of the patient. Thus, with the drug delivery system produced according to the present invention, an API can be administered in a controlled manner, depending on the particular therapy or application case.

The method for producing a drug delivery system according to the present invention comprises the step of screen-printing a base paste. The base paste may include water, polyvinylpyrrolidone, citric acid, hypromellose, stearate, silic acid, glycerol, Hydroxypropyl cellulose, hydroxypropyl methylcellulose, starch, cellulosecrosscaramelose, glycol, crystalline gelatin, collagen, hydroxyapatite, hydrocarbonate, lactide, lactic acid, silica, polaxamers, xylitol, erythritol, ethanol, isopropanol, triacetin, aspartame, sodium bicarbonate, and/or acetone. The viscosity of the base paste may be in the range of $1 \cdot 10^{-2}$-$1 \cdot 10^{14}$ mPa·s, preferably in the range of $1 \cdot 10^{-1}$-$1 \cdot 10^{8}$ mPa·s, further preferred in the range of $1.10^{0}$-$1 \cdot 10^{7}$ mPa·s, further preferred in the range of $1 \cdot 10^{1}$-$1 \cdot 10^{6}$ mPa·s. For screen-printing the base paste, a respective printing mesh may be used, which allows for providing the base paste in accordance with a desired printing profile, so that for example only certain areas of the resulting drug delivery system are formed of the base paste.

Furthermore, the method comprises the step of curing the base paste. Thereby, the base paste may be cured, such that it hardens. The curing temperatures and curing times may depend on the composition of the base paste. For example, the base paste may be cured at a temperature of 30° C. to 180° C., preferably 35° C. to 150° C., further preferred 40° C. to 110° C., further preferred 45° C. to 90° C., further preferred 50° C. to 70° C. Preferably, curing times of 10 seconds to 1 hour, preferably 30 seconds to 30 minutes, preferably 1 minute to 10 minutes may be applied.

Furthermore, the method comprises the step of screen-printing a first paste separate to the (preferably cured) base paste. Thus, the first paste is provided separate from the base paste. Thereby, the first paste is arranged separate from the base paste, i.e. preferably without an overlap, as the first paste may be screen-printed such that it is arranged at locations where the base paste was not screen-printed. The component(s) of the first paste are not mixed with the component(s) of the base paste in a classical manner to form a homogeneous mixture. Instead, the first paste is provided separate to the base paste. Thus, within the resulting drug delivery system, the base paste can be distinguished from the first paste. The first paste may include water, polyvinylpyrrolidone, citric acid, hypromellose, stearate, silic acid, glycerol, Hydroxypropyl cellulose, hydroxypropyl methylcellulose, starch, cellulosecrosscaramelose, glycol, crystalline gelatin, collagen, hydroxyapatite, hydrocarbonate, lactide, lactic acid, silica, polaxamers, xylitol, erythritol, ethanol, isopropanol, triacetin, aspartame, sodium bicarbonate, and/or acetone. The viscosity of the base paste may be in the range of $1 \cdot 10^{-2}$-$1 \cdot 10^{14}$ mPa·s, preferably in the range of $1 \cdot 10^{-1}$-$1 \cdot 40^{8}$ mPa·s, further preferred in the range of $1 \cdot 10^{0}$-$1 \cdot 10^{7}$ mPa·s, further preferred in the range of $1 \cdot 10^{1}$-$1 \cdot 10^{6}$ mPa·s. For screen-printing the first paste, a respective printing mesh may be used, which allows for providing the first paste in accordance with a desired printing profile, so that for example only certain areas of the resulting drug delivery system are formed of the first paste.

Furthermore, the method comprises the step of curing the first paste. The curing temperatures and curing times may depend on the composition of the first paste. For example, the first paste may be cured at a temperature of 30° C. to 180° C., preferably 35° C. to 150° C., further preferred 40° C. to 110° C., further preferred 45° C. to 90° C., further preferred 50° C. to 70° C. Preferably, curing times of 10 seconds to 1 hour, preferably 30 seconds to 30 minutes, preferably 1 minute to 10 minutes may be applied. The first paste may be cured together with the base paste. Alternatively, the screen-printing and curing of the first paste may be performed after curing the screen-printed base paste.

Furthermore, according to the present invention, the first paste comprises a therapeutically effective amount of a first active pharmaceutical ingredient. Accordingly, the first paste may comprise the API which is to be delivered or administered by means of the resulting drug delivery system. The first API may be homogeneously distributed within the first paste. The person skilled in the art understands that the first paste may comprise several APIs, which may be homogeneously distributed within the first paste. Also, the base paste may comprise an active pharmaceutical ingredient.

The method thus allows for producing and enhanced drug delivery system, whereby the base paste and the first paste may be provided in the drug delivery system such that it is possible to obtain a particularly desired release of the first API. By controlling the arrangement of the first paste in relation to the base paste during the respective screen-printing steps, e.g. by choosing proper printing profiles, it can be controlled at what time and at which rate the first API is released from the drug delivery system. This allows for producing a drug delivery system with an optimal API release for a controlled administration of a given API to a body.

The utilization of the screen-printing technique allows for the mass production of the drug delivery system, at a high precision. For example, nano-sized geometries of the first paste, and thus of the first API, can be printed, so that the arrangement of the first API throughout the resulting drug delivery system can be controlled at high precision. The screen-printing technique further allows for providing the first paste such that is forms a particularly preferred geometrical shape in the cured state in the resulting drug delivery system. The utilization of the screen-printing technique further allows for producing several drug delivery systems in a parallel manner. For example, while screen-printing the base paste, numerous drug delivery systems may be produced simultaneously by using a respective printer with such a mesh which allows for printing the base paste to form an array of 100×100 tablets, for example. Similarly, also the first paste may be printed to eventually form the array of 100×100 tablets simultaneously. The array of 100×100 tablets may also be cured simultaneously.

The resolution of the screen-printing pattern depends on the composition of the pastes, among others. Preferably, a resolution in the range of 10 dpi to 10000 dpi, further preferred 100 dpi to 5000 dpi, further preferred 200 dpi to 2000 dpi, further preferred 500 dpi to 1000 dpi is provided for, such that the first API can eventually be arranged in the drug delivery system in a refined manner. Accordingly, two- or three-dimensional structures formed of the base paste and first paste in the drug delivery system may feature a resolution in the range of 10 dpi to 10000 dpi, further preferred 100 dpi to 5000 dpi, further preferred 200 dpi to 2000 dpi, further preferred 500 dpi to 1000 dpi.

Preferably, the drug delivery system is produced layer-by-layer. Thus, in producing the drug delivery system in a layer-by-layer fashion, one layer may be formed on top of another layer to build up the drug delivery system. For example, a first layer of the drug delivery system may be produced by screen-printing and curing the base paste and the first paste, and then a further layer may be produced on top of the first layer, and so on. The drug delivery system may be produced using a movable platform, which may be provided underneath a printing screen. After each completion of a layer, the movable platform may be lowered vertically by a respective step size, and then the next layer may be produced on top thereof. The person skilled in the art understands that the arrangement of the (possibly cured) first paste relative to the (possibly cured) base paste may differ in adjacent layers.

In a preferred embodiment, the pastes are screen-printed such that a resulting planar layer of the drug delivery system comprises both the cured base paste and the cured first paste. Accordingly, a planar layer of the resulting drug delivery system may comprise the cured base paste, and the cured first paste separate to the base paste.

Thus, both (cured) pastes can be differentiated from another, as no homogeneous mixture is provided.

Further preferred, the planar layer of the drug delivery system is produced by screen-printing and curing the base paste to partially form the planar layer, and screen-printing and curing the first paste separate to the base paste to partially form the planar layer. Preferably, by producing the planar layer, the pastes are not screen-printed in an overlapping manner. Thus, by screen-printing and curing the base paste, a part of the resulting planar layer may be formed. A further part of the resulting planar layer, preferably the remaining part of the resulting planar layer, may then formed by screen-printing and curing the first paste. For example, the resulting planar layer may thus comprise areas where only the base paste is arranged (for example at outer regions of the layer), and further areas where only the first paste is arranged (for example at inner regions of the layer). The pastes must not form continuous areas, but can form separate areas, i.e. "islands".

Further preferred, after finishing the production of the planar layer, a further planar layer is produced on top of the finished planar layer. Thereby, a different arrangement or printing-profile may be chosen. Thus, a desired three-dimensional arrangement of the first paste relative to the base paste can be obtained, so that eventually a desired three-dimensional distribution of the first API throughout the resulting drug delivery system can be obtained.

Preferably, the base paste is screen-printed using a screen-printer, and the first paste is screen-printed using a separate screen-printer. Thus, in a respective production line, several screen-printers may be arranged, which are each configured for printing a single paste, for example the base paste or the first paste. By inserting or removing individual printers into or out of the production line, the production line can be modified to produce different drug delivery system designs according to the present invention. Thus, a high flexibility is arranged for by this modular setup.

Preferably, the base paste and the first paste are cured with a shared curing device. Accordingly, only one curing device is preferably needed in the production line, for producing the drug delivery system. Although several individual screen-printers may be used, the built may be transferred to the shared curing device for curing the respective paste(s). This may allow for cost savings.

Preferably, the (cured) base paste and the (cured) first paste are soluble in body fluids. As an example, body fluids may include blood, or body tissue fluids. Body fluids encountered will vary according to the route of administration. Upon oral intake of the drug delivery system, the composition of the outer layer may determine whether dissolution of the drug delivery system will start in the mouth (dissolution in saliva) or later along the journey of the drug delivery system through the gastrointestinal tract, in particular the stomach (acidic milieu), the ileum, the jejunum or other places. Likewise, the drug delivery system produced according to the present invention may be directly placed into tissues (e.g. subcutaneously, intramuscularly) or body cavities (e.g. pleural space) or into the cerebrospinal fluid spaces. Upon placement into the ventricles, the drug delivery system may dissolve within the cerebrospinal fluid and any released API may reach the brain tissue. Placement into natural body cavities (e.g. pleural space, peritoneal space) is meant to reach these localizations at high quantities. Another possibility may comprise dissolution within the airways upon inhalation. The person skilled in the art will appreciate that dissolution characteristics of the (cured) pastes and thus of the resulting drug delivery system may be chosen such that a suitable release of the API is obtained depending on the respective therapy or application. Thereby, a rather instant or rather slow dissolution can be chosen.

The (cured) first paste and the (cured) base paste may dissolve in a similar manner. Preferably, both the base paste and the first paste can dissolve in the same body fluid. Therefore, by screen-printing the first paste and the base paste separate to one another, and due to the dissolution characteristics thereof, it can be controlled at what time and at which rate the first API is released from the resulting drug delivery system. Preferably, the release of the API is determined only by the dissolution characteristics of the (cured) pastes and the form or shape of the resulting drug delivery system. No further release agents are required, such as, e.g., osmotic agents for releasing the API.

Preferably, the pastes are screen-printed such that in the resulting drug delivery system, the (cured) first paste is inhomogeneously arranged in the (cured) base paste. Accordingly, the base paste and the first paste are not provided as a homogeneous mixture in the resulting drug delivery system, but are provided separately from another, preferably in a particular manner, wherein the first paste is inhomogeneously arranged in the base paste. The first paste may be provided inhomogeneously or discontinuously along one, two or most preferred three spatial or orthogonal directions in the base paste. By arranging the pastes in this manner, the first paste is being arranged in the resulting drug delivery system in such a controlled and desired manner, so that no homogeneous distribution of the first paste (and thus of the first API) is present throughout the resulting drug delivery system. Instead, the inhomogeneity is specifically constituted by the particular arrangement of the pastes. As the base paste and the first paste are provided as separate pastes by separately screen-printing the base paste and the first paste in a preferably non-overlapping manner, the first paste can be arranged inhomogeneously within a matrix formed of the base paste. For example, the amount of the first paste arranged within the base paste may increase gradually along a particular direction throughout the resulting drug delivery system.

The pastes may be screen-printed such that in the resulting drug delivery system, the (cured) base paste may be provided or considered as a three-dimensional body, and the (cured) first paste may be inhomogeneously arranged throughout the base paste. Thus, the main body of the resulting drug delivery system may be formed of the base paste and one or more particular parts of the drug delivery system, which may be only of marginal size, may be formed of the first paste. The base paste and the first paste may be arranged on a virtual two- or three-dimensional grid, wherein each pixel of the grid may be occupied by the base paste or by the first paste. Thus, the first paste is preferably arranged inhomogeneously in the base paste and thus may be inhomogeneously arranged in the resulting drug delivery system itself. The size or volume of each of such a pixel may be in the range of 1 $\mu m^3$ to 1 $cm^3$, preferably in the range of 10 $\mu m^3$ to 100 $mm^3$, preferably in the range of 100 $\mu m^3$ to 10 $mm^3$, and most preferred of about 1 $mm^3$.

As the common principle of a homogeneous distribution of an API throughout the drug delivery system is preferably suspended, it is possible to provide a particular arrangement of the API in the resulting drug delivery system to obtain a drug delivery system with a customized release profile of the API. The paste comprising the API may be arranged such that a steady release of the API is obtained, with a release that preferably results in a blood-tissue concentration slightly above the efficacy threshold of the API. Thereby, as compared to the commonly produced drug delivery systems with a homogeneous distribution of the API, an effectively less amount of API is advantageously required with the preferred drug delivery system produced according to the present invention, while the same clinical results are maintained with lower side-effects.

Preferably, the inhomogeneous distribution of an API in the drug delivery system produced according to the present invention is utilized in a standardized manner, whereby a particular arrangement is chosen or set. This concept allows for producing drug delivery systems with the advantageous release profiles as described herein. The standardization, definition or specification of the arrangement of the pastes and thus, the standardization, definition or specification of the inhomogeneity of the API allows for producing such drug delivery systems uniformly in high quantity, also in a mass production.

The person skilled in the art understands that by screen-printing and curing the base paste, processes such as cross-linking within the base paste may take place, thereby eventually altering the base paste itself. It will be appreciated that the resulting structure of the cured base paste may still be considered to be essentially formed of the respective base paste, although its viscosity may have changed significantly. Accordingly, when reference is made to the base paste in the resulting drug delivery system, the person skilled in the art understands that this base paste may be the respective cured base paste. The same applies to other pastes.

In a preferred embodiment, the pastes are screen-printed such that in the resulting drug delivery system the concentration of the first API varies throughout the drug delivery system, or further preferred varies throughout the body defined by the base paste. For example, printing profiles may be chosen which allow for screen-printing the first paste at central parts of the drug delivery system only. Thus, particular regions of the resulting drug delivery system may be identified having a rather high concentration of the first API, and particular regions may be identified having a rather low (or even no) concentration of the first API. Thereby, whilst taking into consideration the particular form or shape of the drug delivery system, as well as the dissolution characteristics of the base paste and first paste, it can be precisely controlled when and how the API is eventually released.

Further preferred, the pastes are screen-printed such that in the resulting drug delivery system the concentration of the first API is highest at a center, at an edge or at an intermediate region of the drug delivery system. Thus, for example, if the resulting drug delivery system is provided in form of a tablet, the first paste may be arranged or screen-printed such that a peak concentration of the first API is provided at the center or a central part of the tablet. Accordingly, upon administration of the tablet and dissolution of the base paste and the first paste, the release of the first API may increase over time, or may remain approximately constant over time, also depending on the shape of the drug delivery system. This allows for obtaining a desired, specific release of the API.

Further preferred, the pastes are screen-printed such that in the resulting drug delivery system a gradient of the concentration of the first API increases towards or increases away from a center of a drug delivery system. For example, the printing profiles may be chosen such that the amount of screen-printed first paste increases towards the center of the drug delivery system. For example, if the resulting drug delivery system is provided in form of a spherical tablet, the arrangement of the first paste and thus of the first API may be such that the release rate is approximately constant upon application of the drug delivery system, when the concentration increases towards the center of the tablet. By adjusting the concentration profile of the API throughout the drug delivery system by adjusting the printing profile during screen-printing, the release profile of the API can be well controlled.

Further preferred, the pastes are screen-printed such that in the resulting drug delivery system a concentration profile of the first API throughout the drug delivery system comprises a smooth transition to an area of increased concentration. For example, the printing profiles may be chosen such that the amount of screen-printed first paste increases gradually towards the center of the drug delivery system. Thus, the concentration profile may comprise a smooth transition between an area of low (or possibly no) concentration, and an area of high concentration. A smooth transition may be defined by the absence of abrupt or discontinuous steps in the concentration profile.

The concentration profile may represent the profile of the concentration of the first API diagonally across the resulting drug delivery system, for example from one edge of the drug delivery system to its center, or possibly extending through the entire drug delivery system. With such smooth transitions, it is possible to obtain a smooth onset of the release of the API upon dissolution of the respective cured paste.

Further preferred, the pastes are screen-printed such that in the resulting drug delivery system a concentration profile of the first API throughout the drug delivery system comprises more than one area of increased concentration. Thereby, several dosages of the API can be administered over time with the resulting drug delivery system. Particularly preferred, due to the respective printing profiles during a screen-printing, the deposition of the first API within the drug delivery system along the dissolution direction (e.g. from the periphery to the center) may be discontinuous and repetitive in an onion skin type manner. In each such shell of the drug delivery system, the first paste may be provided inhomogeneously, such that a release of the first API is preferably not starting in an abrupt manner, but can be set such that the release starts and/or ends gradually. Thereby, the release of the API may occur in distinct waves, intervals with high release of the first API are followed by intervals with low or no release. Further, the API can be administered in several phases over time. These phases (and in particular their onset) can be controlled by controlling the arrangement of the areas of increased concentration within the drug delivery system, by choosing or adjusting the respective printing profiles during screen-printing.

Further preferred, the pastes are screen-printed such that in the resulting drug delivery system the variation of the concentration of the first API throughout the system is at least 5%, further preferred at least 10%, further preferred at least 15%, further preferred at least 20%, further preferred at least 25%, further preferred at least 30%, further preferred at least 35%, further preferred at least 40%, further preferred at least 45%, further preferred at least 50%, further preferred at least 55%, further preferred at least 60%, further preferred at least 65%, further preferred at least 70%, further preferred at least 75%, further preferred at least 80%, further preferred at least 85%, further preferred at least 90%, further preferred at least 95%, further preferred approximately 100%. Further preferred, the pastes are screen-printed such that in the resulting drug delivery system the variation of the concentration of the first API throughout the system is at most approximately 100%, further preferred at most 95%, further preferred at most 90%, further preferred at most 85%, further preferred at most 80%, further preferred at most 75%, further preferred at most 70%, further preferred at most 65%, further preferred at most 60%, further preferred at most 55%, further preferred at most 50%, further preferred at most 45%, further preferred at most 40%, further preferred at most 35%, further preferred at most 30%, further preferred at most 25%, further preferred at most 20%, further preferred at most 15%, further preferred at most 10%, further preferred at most 5%. Thus, the variation of the concentration can be set in a controlled manner, by providing a respective local arrangement of the first paste relative to the base paste with the screen-printing technique, to eventually obtain a desired controlled administration of the first API with the resulting drug delivery system. The variation of the concentration of the first API may be defined as the difference of the maximum concentration and the minimum concentration of the API in the drug delivery system. In this context, the concentration may be the mass-specific concentration. The respective sampling volume for measuring the concentration may be any suitable volume, and may for example be of 1 $\mu m^3$. For example, if the highest concentration in a sampling volume in the drug delivery system is of about 80%, and the lowest concentration in a sampling volume in the drug delivery system is of about 10%, then the variation may be 70%. Thus, for example, throughout the drug delivery system, the concentration of the first API may be at least 10%, and at a central part of the drug delivery system, the concentration of the first API may increase to 80%.

Further preferred, the pastes are screen-printed such that in the resulting drug delivery system the concentration profile of the first API is such that upon application of the system, the first API is released from the system at a predetermined release profile, which further preferred comprises a section with a release at a constant rate. Accordingly, the first paste may be arranged such within the base paste due to the particular screen-printing profiles that upon application of the resulting drug delivery system, and upon dissolution of the (cured) base paste and (cured) first paste, a particular release profile of the API is obtained, with a constant release section in a preferred embodiment.

Particularly preferred, the pastes are screen-printed such that in the resulting drug delivery system the first paste is arranged in the base paste such that upon dissolution of the drug delivery system or the (cured) pastes, the total amount of the first API at an outer surface of the drug delivery system remains approximately constant for a predetermined time, wherein the predetermined time is preferably in the range of 1 second up to 180 days. For example, printing profiles may be chosen which allow for screen-printing the first paste such that the amount of printed first paste increases towards central parts of the drug delivery system only. The person skilled in the art understands that depending on the respective application and the form of the drug delivery system, rather longer or rather shorter release periods may be applicable. For example, if the drug delivery system is produced in form of an implant, the API may be release during an extended period of up to 180 days. If the drug delivery system is produced in form of a tablet, for example, the API may be released during a period of up to 12 hours. Accordingly, further preferred, the predetermined time of approximately constant release is in the range of 5 seconds to 24 hours, further preferred 10 seconds to 12 hours, further preferred, 1 minute to 6 hours, further preferred 10 minutes to 1 hour. Accordingly, in the exemplary case of a spherical tablet, a gradient of the concentration of the first API may point inwards, so that the amount of API at the surface of the drug delivery system remains constant when the drug delivery system is dissolving, i.e. when the volume and surface of the system shrinks. Hence, the first paste may be arranged such that eventually the concentration of the first API depends on the distance to the surface of the drug delivery system. Accordingly, by inhomogeneously arranging the first paste in the base paste with the screen-printing technique, a constant release of the first API can be set.

Further preferred, the pastes are screen-printed such that in the resulting drug delivery system the concentration profile of the first API is such that upon application of the system, the first API is released at two or more dosages, wherein release of the first API at one of the dosages starts preferably 1 second to 10 days (the upper value may for example apply if the drug delivery system is produced in the form of an implant), more preferably 2 seconds to 1 day, more preferably 5 seconds to 12 hours, more preferably 10 seconds to 6 hours, more preferably 20 seconds to 2 hours, more preferably 1 minute to 1 hour, and most preferred 10 minutes to 30 minutes before release of the first API at another one of the dosages. For example, printing profiles may be chosen such that the first paste is provided at several, separated locations towards a center of the drug delivery system. Thus, for example, if the drug delivery system is provided in form of a tablet, and upon oral administration of the tablet, the first API may be released at a first dosage shortly after administration, before the first API is released at a second dosage at a later time. The dosages may be uniform or may vary among each other. Any duration of release of an API mentioned herein may be measured by means of dissolution tests, for example according to USP-Guideline "General Chapter <711> Dissolution".

In a further preferred embodiment, the pastes are screen-printed such that in the resulting drug delivery system the base paste envelops the system and the first paste is not arranged at an outer face of the system. Accordingly, the first paste comprising the first API may be provided such that it cannot be accessed from the outside, at least prior to the application of the drug delivery system. Thus, the first API can be effectively sealed from the environment, reducing the risk of contamination. Furthermore, if for example produced in form of a tablet, the dissolution of the first paste is delayed upon oral administration, as the base paste has to (at least partially) dissolve first. Thus, a delayed administration of the first API can be obtained. Preferably, the drug delivery system is produced such that release of the first API starts 1 second to 1 day, further preferred, 10 seconds to 12 hours, further preferred 30 seconds to 6 hours, further preferred 1 minute to 4 hours, further preferred 10 minutes to 2 hours, further preferred 30 minutes to 1 hour after application of the drug delivery system.

In a further preferred embodiment, the method further comprises the steps of screen-printing a second paste separate to the base paste and the first paste, and curing the second paste. The second paste may comprise a therapeutically effective amount of a second active pharmaceutical ingredient. Accordingly, the method allows for producing a drug delivery system characterized by a controlled administration of several APIs in particular applications. The APIs may interact after dissolution of the respective paste, and may thereby provide for a synergetic effect in the body. The first and second API may differ in form as well as in concentration. Preferably, the (cured) second paste is soluble in body fluids. The respective provisions given with reference to the first paste and the base paste similarly apply here.

The person skilled in the art understands that the provisions given herein with regard to the screen-printing and curing steps of the base paste and first paste, as well as the provisions regarding the first API may similarly apply in an analogous manner to the second paste and the second API. The person skilled in the art understands that the method may comprise further steps of screen-printing and curing further pastes comprising further active pharmaceutical ingredients, e.g. a third paste comprising a third API, a fourth paste comprising a fourth API, and so on.

Particularly, the pastes are screen-printed such that a resulting planar layer of the drug delivery system comprises all of the cured base paste and the cured first paste and the cured second paste. Accordingly, a planar layer of the resulting drug delivery system may comprise the cured base paste, and the cured first paste separate to the base paste, and the cured second paste separate to the base paste and the first paste. Thus, all the (cured) pastes can be differentiated from another, as no homogeneous mixture is provided.

Further preferred, the planar layer of the drug delivery system is produced by screen-printing and curing the base paste to partially form the planar layer, screen-printing and curing the first paste separate to the base paste to partially form the planar layer, and screen-printing and curing the second paste separate to the base paste and the first paste to partially form the planar layer. Preferably, by producing the planar layer, the pastes are not screen-printed in an overlapping manner. Thus, by screen-printing and curing the base paste, a part of the resulting planar layer may be formed. A further part of the resulting planar layer may then be formed by screen-printing and curing the first paste. A further part of the resulting planar layer, preferably the remaining part of the resulting planar layer, may then be formed by screen-printing and curing the second paste. For example, the resulting planar layer may thus comprise areas where only the base paste is arranged (for example at outer regions of the layer), areas where only the first paste is arranged (for example at inner regions of the layer), and areas wherein only the second paste is arranged (for example at intermediate regions of the layer). The pastes must not form continuous areas, but can form separate areas, i.e. "islands".

Preferably, the pastes are screen-printed such that in the resulting drug delivery system the (cured) second paste is inhomogeneously arranged in the (cured) base paste. Thus, the release of the first API and the second API from the drug delivery system can be controlled also relatively to each other by controlling the inhomogeneous arrangement of the respective first and second pastes in the base paste. The above explanation with regard to the inhomogeneous arrangement also applies here.

Further preferred, the pastes are screen-printed such that in the resulting drug delivery system a concentration profile of the first API throughout the drug delivery system is different than a concentration profile of the second API throughout the drug delivery system. For example, printing profiles may be chosen such that the amount of screen-printed first paste increases towards a center of the drug delivery system and the amount of screen-printed second paste decreases towards the center of the drug delivery system. Accordingly, the drug delivery system can be designed and produced such that the first API and the second API are released to the body at different dosages.

Further preferred, the pastes are screen-printed such they are eventually arranged in a discontinuous manner within the resulting drug delivery system such that the first active is released for a distinct period of time upon the start of the dissolution of the drug delivery system, which typically occurs from the periphery. Similar to an onion skin type arrangement, the layer with the first paste may be adjacent to another layer containing either no API or the second API, for example. By varying parameters like the thickness of the layers, their composition, and the distribution of the APIs within the layers, the release of the APIs may be controlled.

Further preferred, the pastes are screen-printed such that in the resulting drug delivery system the first paste and the second paste are arranged such that upon application of the drug delivery system, release of the first API starts before release of the second API. For example, printing profiles may be chosen such that the second paste is printed closer to the center of the drug delivery system, while the first paste is printed further to the edge of the drug delivery system. The release of the first API may further preferred start 1 second to 10 days (the upper value may for example apply if the drug delivery system is produced as an implant), more preferably 2 seconds to 1 day, more preferably 5 seconds to 12 hours, more preferably 10 seconds to 6 hours, more preferably 20 seconds to 2 hours, more preferably 1 minute to 1 hour, and most preferred 10 minutes to 30 minutes before release of the second API. Accordingly, due to the particular inhomogeneous or discontinuous arrangement of the first and second pastes in the base paste, preferably with regard to the dissolution direction, it can be controlled at what time the respective first and second APIs are released relative to one another. Depending on the spatial arrangement of the first and second APIs within the layers, the release of the two APIs may be separated by a defined time interval or the release of the first API may continue when the release of the second API starts. Thereby, particular synergetic effects of the APIs may be obtained. Generally, the APIs may be released to the body within hours, days and months, depending on the individual form of application.

Preferably, the pastes are screen-printed such that in the resulting drug delivery system the first paste and the second paste are arranged such that upon application of the drug delivery system, a release profile of the first API differs from a release profile of a second API. For example, the first API may be released at a rather constant rate, while the second API may be released intermittently. This allows for designing an elaborate drug delivery system.

In a preferred embodiment, the total amount of the first API in the first paste in the resulting drug delivery system is between 1 μg and 100 g, preferably between 10 μg and 10 g, more preferably between 100 μg and 1 g, more preferably between 500 μg and 500 mg, more preferably between 1 mg and 100 mg, more preferably between 10 mg and 50 mg. The person skilled in the art understands that any description with regard to the first API may also apply to a possible second or further APIs provided in a second or further pastes of the drug delivery system.

In a further preferred embodiment, one or more of the pastes comprises a ceramic, metal, polymer (preferably polymer acrylate) and/or minerals.

In a preferred embodiment, one or more of the pastes comprises a disintegration agent, which may facilitate dissolution of the respective (cured) paste. The disintegration agent may comprise cellulose (preferably microcrystalline cellulose), croscarmelose sodium, crospovidone, starches (preferably modified starches), cross-linked plyvinylpyrrolidone, sodium starch glycolate, and/or sodium carboxymethylcellulose.

Preferably, one or more of the pastes may comprise one or more constituents selected from the following list: colorant, sweetener, flavor, antimicrobial preservative (e.g. sorbic acid, benzoic acid, parabens, scrose, benzalkonium chloride), chemical stabilizers which may be used to increase the chemical stability of the API (e.g. antioxidants such as ascorbic acid or sodium metabisulfite, chelators such as ethylenediaminetetraacetic acid), viscosity modifiers which may be used to reduce the sedimentation of particles (e.g. polymeric materials or inorganic materials such as clay), cellulosic materials which may be used as viscosity enhancers in suspensions (e.g. cellulose, cellulose ethers, alginic acid).

Preferably, one or more of the pastes may comprise one or more excipients selected from the following list: filler (e.g. lactose, sucrose, glucose, mannitol, sorbitol, calcium carbonate, cellulose), solution binder (e.g. gelatin, polyvinylpyrrolidone, cellulose derivative, polyethylene glycol), dry binder (e.g. cellulose, polyethylene glycol, methylcellulose), glidant (e.g. silica, magnesium stearate, talc).

In a preferred embodiment, the first paste is screen-printed to form a geometrical shape. The shape may preferably be a tube (which may be a hollow tube), a spot (which may be a local, small cluster or agglomeration), an oval (e.g. in the shape of an open circle or ellipse), a plate, and/or a polygon (e.g. in the shape of a square). Thus, the first paste may be provided in such a shape that a desired release of the first API is obtained, possibly even with regard to further APIs provided in further pastes of the system. Within the particular geometrical shape, the concentration of the API may vary.

In a preferred embodiment, the resulting drug delivery system is in the form of a tablet, a capsule, a disc, a film, an implant, a subcutaneous implant, a patch, pellets or granules. Thus, the drug delivery system produced according to the present invention may have various forms, and thereby allow for a desired administration and desired release of an API according to the particular therapeutic application.

Preferably, the pastes are screen-printed such that the resulting drug delivery system features a structured surface. For example, the printing profiles may be chosen such that protrusions and recesses are forming the surface of the resulting drug delivery system. Thereby, the surface of the resulting drug delivery system can be enlarged, so that eventually a high release of the respective API can be provided for.

It will be appreciated that the drug delivery system produced according to the present invention is not limited to a particular API. Generally, any suitable API, which can be provided in a respective paste to be inhomogeneously arranged within a base paste, can be used. For example, the API may be any of anti-infectives, anti-inflammatories, cardioactive agents, neuroleptic agents, or even nutritional agents. The skilled person understands that this list is not limiting. Further, the drug delivery system produced according to the present invention may comprise further components or substances, for example additives or the like.

In a preferred embodiment, the first API may be any of anthelmintic agents, narcotics and narcotic antagonists; antihistamines, adrenergic agents, adrenergic blockers sedative hypnotics, CNS agents, analeptics, antiparkinson agents, steroids, coronary vasodilators, anticoagulants, antihypercholesterolemics, antibiotics, antifungal agents, antiviral agents, bone growth promotants, anticancer agents, vitamins, antiinflammatory agents, or antihypertensive agents. In a preferred embodiment, the first API may comprise Pregabalin, Lurasidon, Fentanyl, Rivaroxaban, Sildenafil/Tadalafil, Desatinib, Sorafenib, Varenicline, Memantine, Dexlansoprazole, Sunitinib, Nebivolol, Zolmitriptan, Sitagliptin, Lacosamid, Desvenlafaxin, Lenalidomid, Ledipasvir/Sofosbuvir, Aripiprazole, Levodopa, or Ondansetron/Granisetron. Again, the skilled person understands that this list is not limiting.

The present invention further relates to a drug delivery system produced with a method as described herein.

Furthermore, the present invention relates to a system for producing a drug delivery system. The system (or production system) thereby comprises means for producing a drug delivery system in a manner as described herein. A production system for producing a drug delivery system according to the present invention may thereby comprise means for screen-printing a base paste, means for curing the base paste, means for screen-printing a first paste separate to the base paste, and means for curing the first paste. Again, the first paste thereby comprises a therapeutically effective amount of a first API. The person skilled in the art understands that within the concept of the present invention, the production system may further comprise means for screen-printing a second paste comprising a therapeutically effective amount of a second API, for example.

5. BRIEF DESCRIPTION OF THE SEVERAL VIEWS OF THE DRAWINGS

Figure 2:
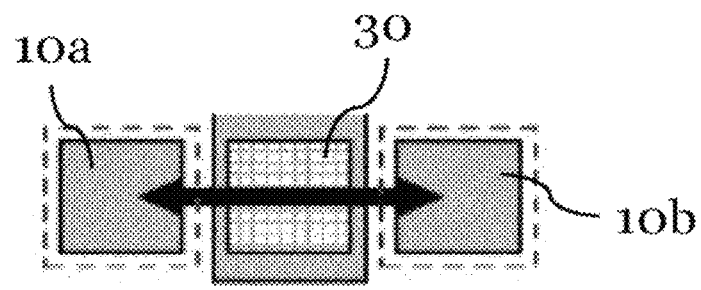
Figure 3:
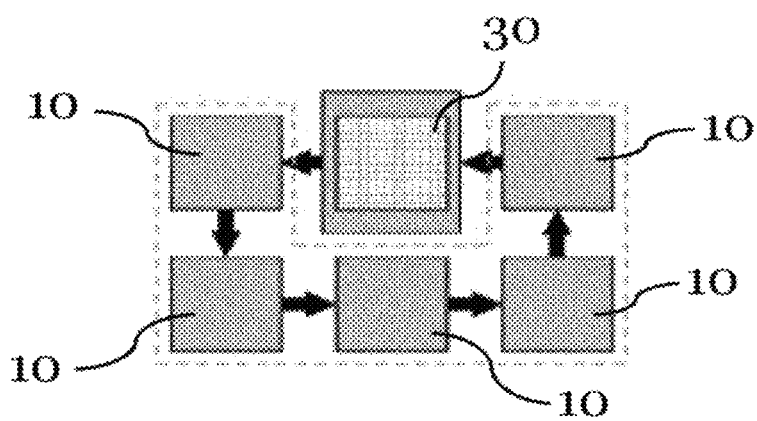
Figure 4:
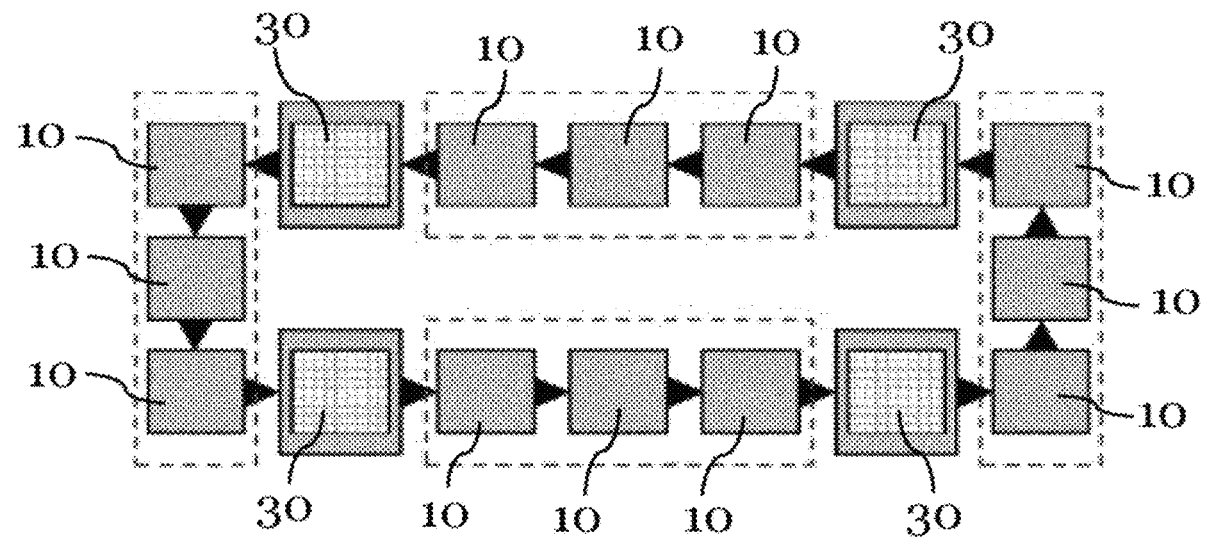
Figure 5:
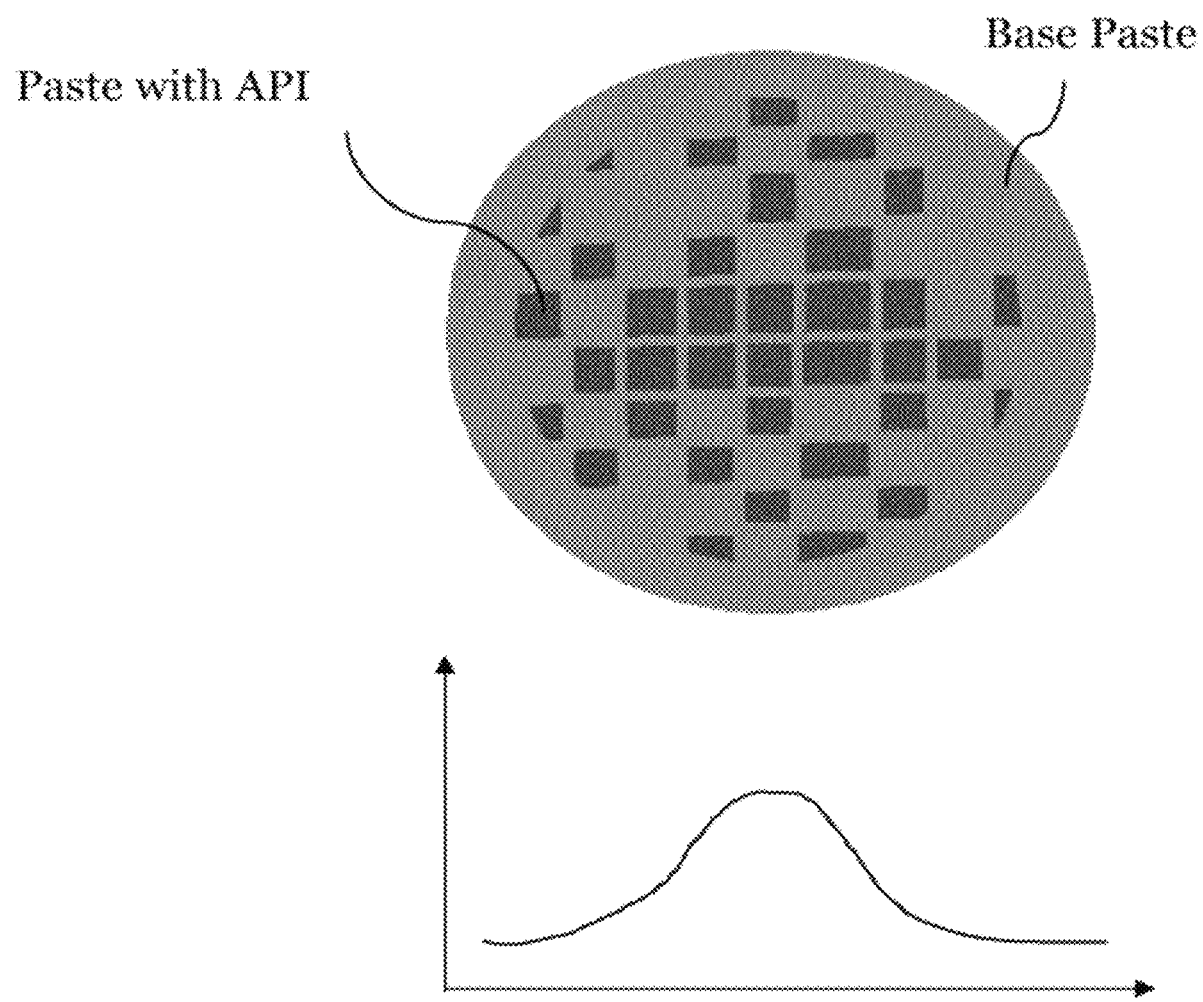
Figure 10:
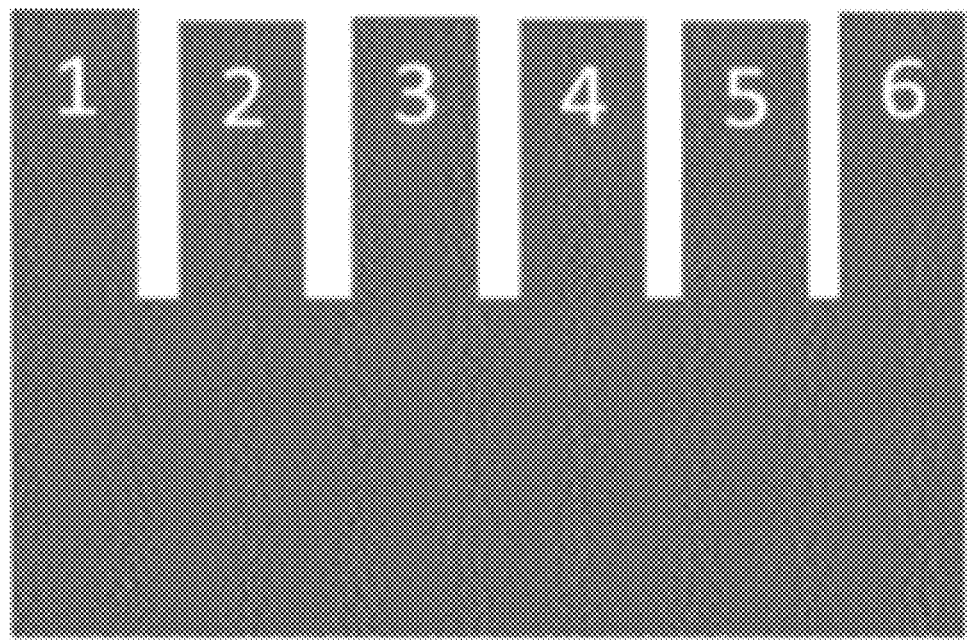

In the following, the present invention will be described with reference to the enclosed figures. Thereby, similar features are provided with equal reference signs. It shows:

FIGS. 1A-D illustrate the operation of a part of a production system for producing a drug delivery system according to the present invention;

FIG. 2 a first design of a production system for producing a drug delivery system according to the present invention;

FIG. 3 a second design of a production system for producing a drug delivery system according to the present invention;

FIG. 4 a third design of a production system for producing a drug delivery system according to the present invention;

FIG. 5 a design of a drug delivery system produced according to the present invention and the respective concentration profile;

FIGS. 6A-C several API release profiles of drug delivery systems produced according to the present invention wherein FIG. 6A represents the release profile when the API is homogeneously distributed throughout the drug delivery system, FIG. 6B represents the release profile when the API is arranged at an edge of the drug delivery system and FIG. 6C represents the release profile when the API is accumulated at a central part of the drug delivery system;

FIGS. 7A-I further designs of drug delivery systems produced according to the present invention comprising a base paste, pastes A-D, and an additive;

FIGS. 8J-M further designs of drug delivery systems produced according to the present invention;

FIG. 9 another design of a drug delivery system produced according to the present invention; and FIG. 10 a structured drug delivery system produced according to the present invention.

6. DETAILED DESCRIPTION

FIG. 1 illustrates a part of a production system for producing a drug delivery system according to the present invention. As can be seen, a screen 10 is provided, which allows for screen-printing pastes in the sense of the present invention, for example a base paste. Therefore, the screen 10 comprises a respective mask ii, which masks particular parts for screen-printing a desired pattern, according to a respective printing profile. Furthermore, the screen 10 comprises a blade 13 which can draw the material or paste 12 to be printed over the screen, and in particular over the mask ii.

As can be seen in FIG. 1A, a movable platform 20 is provided beneath the screen 10. A particular built 40 is already present on the platform 20, which may have been produced layer-by-layer according to the present invention.

Figure 1B:
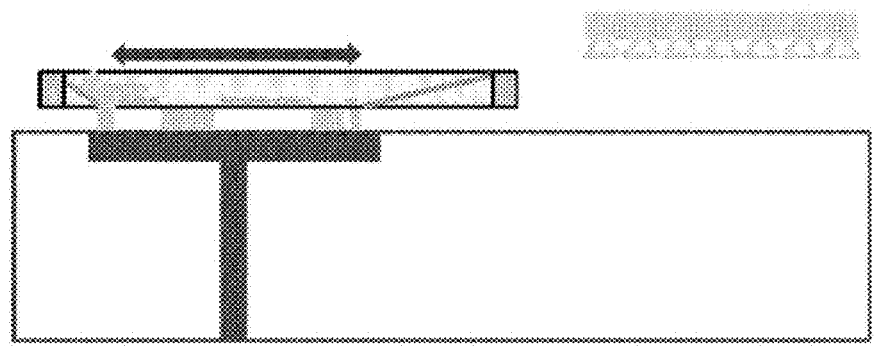

As can be seen in FIG. 1B, the blade 13 can draw the paste 12 along the screen 10, such that a further layer of the paste 12 is screen-printed onto the built 40. As the mask ii masks several parts, the paste 12 is printed only at particular locations on the built 40. Thus, the arrangement of the paste 12 within the resulting drug delivery system can be precisely controlled.

Figure 1C:
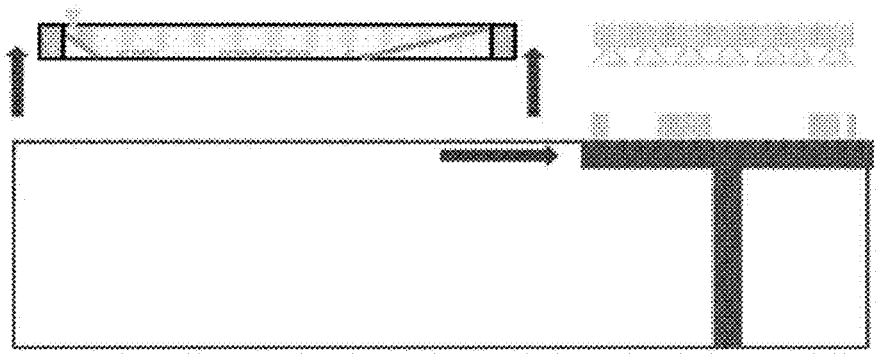

Afterwards, as can be seen in FIG. 1C, the screen 10 is uplifted, and the platform 20 with the built 40 comprising the additional layer of a screen-printed paste moves horizontally to place the built 40 underneath a dryer 30. By means of this dryer 30, the screen-printed layer is cured. Thereby, the printed paste may harden.

Afterwards, the platform 20 may be moved to another screen at another printing station, to complete further parts of the layer by screen-printing and curing further pastes.

Figure 1D:
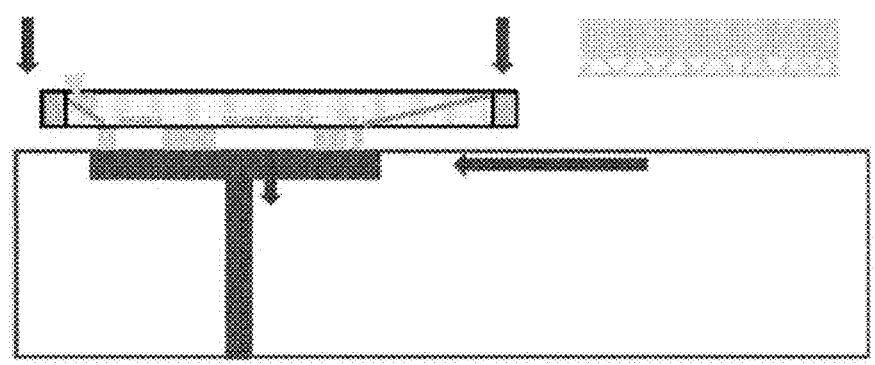

After completion of the layer, the platform may be returned to the illustrated printer and screen 10, as illustrated in FIG. 1D, to print the respective paste 12 on top of the built 40. The height of the platform 20 is lowered by an amount which corresponds to the thickness of the previously build layer, and the screen 10 is moved to its lower printing position so that a further layer can be provided on top of the cured layer.

FIGS. 2-4 show different design concepts of production systems for producing a drug delivery system according to the present invention. In FIG. 2, two screen-printers 10a, 10b are arranged with a dryer 30 in between. With the printer 10a, a base paste according to the present invention may be printed, which may then be cured by means of the dryer 30, and then a first paste may be printed by means of printer 10b at parts not covered by the base paste. Afterwards, also the first paste may be cured with the dryer 30, before the built is moved back to the first printer boa for starting the production of a new layer. By changing the meshes or printing profiles of the printers 10a, 10b, the three-dimensional layout of the pastes in the resulting drug delivery system can be modified.

According to the concept of FIG. 3, five printers 10 are arranged in addition to a single dryer 30. With each of these printers, different pastes may be screen-printed to eventually form a single, continuous layer, which may then be cured in one step by means of the single dryer 30. Afterwards, a new layer may be produced on top thereof.

According to the design of FIG. 4, several printers 10 may be arranged together with several dryers 30. Thereby, three successive printers 10 may print a first complete planar layer, which is then cured with a respective dryer 30, before a further planar layer is printed on top, which may differ from the previously printed and cured layer.

This procedure may be reiterated with the further printers and dryers, as will be appreciated by the person skilled in the art.

FIG. 5 illustrates a design of a drug delivery system produced according to the present invention. Thereby, a planar layer of the drug delivery system is shown, which may extend through the drug delivery system. Therein, the paste comprising the API and the base paste are arranged on a grid-like structure, with each "pixel" defined either by the API paste or the base paste. As can be seen, the two pastes are arranged such that the density of the "API-pixels" is higher at a central part of the drug delivery system. This is also apparent from the API concentration profile, which is also illustrated in FIG. 5. The profile features a peak of high API concentration at the center of the system, and low API concentration at the edges of the system. The transition from the low API concentration at the edges to the high API concentration at the center is smooth, as it does not feature any abrupt steps. With such a drug delivery system, the release profile of the drug delivery system upon dissolution of the two pastes is adjusted or configured in a desired manner.

FIGS. 6A-C show the release profile of a common drug delivery system with a homogeneously distributed API (FIG. 6A), as well as two release profiles of drug delivery systems produced according to the present invention (FIGS. 6A-C). The design of the respective drug delivery system is shown next to the graphs. The drug delivery systems are provided in a round shape, and may be a tablet dissolving upon oral administration, for example. The respective graphs each show the release of the API of the respective drug delivery system over time.

Regarding FIG. 6A, the design of the respective drug delivery system is such that the API is homogeneously distributed throughout the drug delivery system. This principle of homogeneity, which is the key feature of common prior art drug delivery systems, derives from the corresponding manufacturing processes. Upon dissolution of classical drug delivery systems, the respective API is released. Due to the dissolution characteristics of the homogeneous system and the shape of the drug delivery system, a particular and fixed release profile is obtained. As can be seen from FIG. 6A, the release of the API increases gradually over time, reaches a maximum, and thereafter decreases gradually.

Due to the inhomogeneous arrangement of the API according to the present invention, different release profiles can be obtained. The design associated with FIG. 6B is different from that associated with FIG. 6A, as the API is arranged at an edge of the drug delivery system. Hence, the principle of a homogeneous distribution of the API in the drug delivery system is suspended, as the API is inhomogeneously arranged in the drug delivery system, being provided here with a high concentration at the edge of the drug delivery system. The concentration of the API smoothly decreases towards the center of the drug delivery system. Upon application of the drug delivery system associated with FIG. 6B, the release of the API is rather high in the beginning and then decreases gradually. Such a high initial API release may be beneficial for particular applications, as will be appreciated by the person skilled in the art.

In the design associated with FIG. 6C, the API is accumulated at a central part of the drug delivery system. Thus, the concentration of the API is highest at the center of the system, and the gradient of the concentration points from the edge of the system to its center. As can be seen from the respective FIG. 6C, the release increases approximately gradually over a prolonged period of time, and the maximum release rate is delayed in time as compared to the common design. In comparison to the common design, the release of the API can be considered to be more constant, for an extended period of time. Such a release profile may be beneficial for particular applications, as will be appreciated by the person skilled in the art.

FIGS. 7A-I illustrate nine design options for drug delivery systems produced according to the present invention. As can be seen, all these designs comprise a base paste, which forms the overall body of the respective drug delivery system (DDS) and can be considered as a matrix, within which further pastes may be arranged. These further pastes are labeled as paste A, paste B, paste C and paste D, and may each comprise a therapeutically effective amount of a separate active pharmaceutical ingredient (API). Thus, any of the pastes A-D may be considered as a first paste within the context of the present invention. The base paste and the pastes A-D are soluble in body fluids.

The design of DDS in FIG. 7A has a round shape. DDS in FIG. 7A may be in a form of a tablet, a disc or the like. It has a particular diameter D, which may be, for example, 15 mm. Within the base paste of FIG. 7A, a first paste A comprising a first API, a second paste B comprising a second API and a third paste C comprising a third API are provided. As can be seen, the respective APIs are not distributed homogeneously through the drug delivery system, but are arranged inhomogeneously within the base paste, as the pastes A, B, C are provided at particular positions within the drug delivery system. The pastes A, B, C are provided in a polygonal shape, with a hexagonal cross section.

Upon application of DDS in FIG. 7A and dissolution thereof, the base paste dissolves first, as the dissolution may begin at the edge of the system. After a particular period of time, paste C and then paste B start to dissolve, thereby releasing the respective APIs. Later on, paste A eventually starts to dissolve, thereby releasing the respective first API provided therein. Thus, due to the particular arrangement of the pastes in the drug delivery system, the different APIs are released at different stages at different dosages after application of the drug delivery system. Due to the particular arrangement of the different pastes within FIG. 7A, each API is released at a particular time after application of the drug delivery system, with a particular and individual, API-specific release profile.

The design of DDS in FIG. 7B is formed as a tablet, with a height of, for example, 2.5 mm, and a diameter of again 15 mm. Two pastes B and C comprising each an API are provided within the base paste in an inhomogeneous manner according to the present invention. Upon application of the drug delivery system, particular release profiles of the APIs contained in pastes B and C are obtained, which may feature smooth transitions between phases of increased release.

The design of DDS in FIG. 7C is similar to that of DDS in FIG. 7A, however comprising, beside the base paste, only two pastes B and C comprising each an API. Upon application of the drug delivery system, particular release profiles of the APIs contained in pastes B and C are obtained, which may feature smooth transitions between phases of increased release.

In the design of DDS in FIG. 7D, two pastes with APIs are provided in a tube-like shape. Similarly, the pastes may also be provided in form of stacked plates.

DDS in FIG. 7E has a design where the pastes comprising APIs are provided as spots within the base paste. Upon application of the drug delivery system, particular release profiles of the APIs contained in pastes B and C are obtained, which may feature smooth transitions between phases of increased release.

DDS in FIG. 7F has a design of a particular heights of, for example, 25 mm, wherein only one paste comprising an API is arranged inhomogeneously in the base paste, in a tube-like manner. Similarly, the paste may also be provided in form of plates.

DDS in FIG. 7G is similar to DDS in FIG. 7E, however the pastes comprising APIs are arranged in a more random manner. Upon application of the system, particular release profiles of the APIs contained in pastes B and C are obtained, which may feature smooth transitions between phases of increased release.

DDS in FIG. 7H has a design, where the pastes comprising the APIs are provided or arranged in the form of circles within the base paste. Upon application of the drug delivery system, the base paste and the first paste dissolve in an alternating manner, such that the first API is released intermittently, for example in a rather periodic manner. After the first API is completely released, the second paste starts dissolving, thereby releasing the second API. As can be seen, the circles of paste A are not concentric, and are not having a uniform thickness. Due to this particularly inhomogeneous arrangement, a particular release profile is obtained, which may feature smooth transitions between phases of increased release.

DDS in FIG. 7I has a design where a paste comprising an API is provided in a particular pattern within a matrix of additives, which is arranged in the base paste.

FIGS. 8J-8M show further design options for a drug delivery system produced according to the present invention. The overall shape of the system is that of a round disc with a diameter of 5-25 mm, preferably 20 mm or 15 mm, and a thickness of 0.5-15 mm, preferably 2 mm or 6 mm. A cut into the tablets is provided to allow for a view on the arrangement of the pastes in the tablets.

Figure 8J:
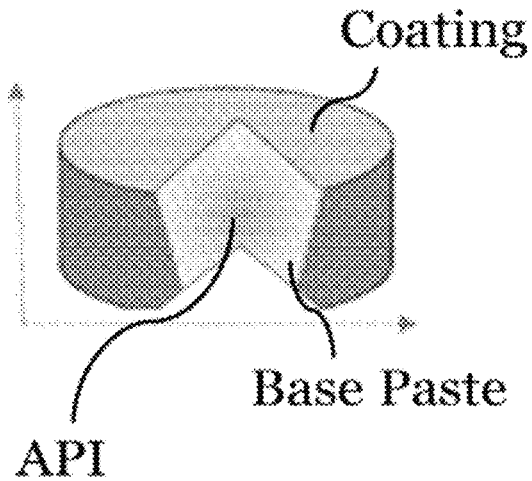

The design of DDS in FIG. 8J has a first paste comprising a first API provided at the central part of the tablet, being surrounded by a base paste, while the entire tablet is coated with a coating. The coating may be a hydrophilic coating, or may provide entericcoated properties, for example. The concentration of the API within the tablet is highest at the center of the tablet. The concentration profile of the API is such that it comprises a smooth transition from the edge of the tablet towards the center of the tablet.

Figure 8K:
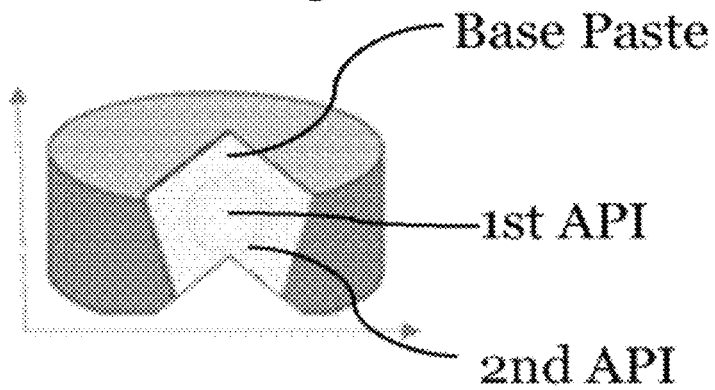

The design of DDS in FIG. 8K has a first paste comprising a first API and a second paste comprising a second API being provided within a base paste. Again, also a coating is provided. The second paste is arranged in the form or a sphere, and the concentration of the second API is highest on the surface of the sphere, decreasing smoothly towards the center of the sphere. Within the sphere formed of the second paste, the first paste is provided. Thus, upon application of the tablet and dissolution of the pastes, the second API is released prior to the first API, and during a transition period, both APIs are released.

Figure 8L:
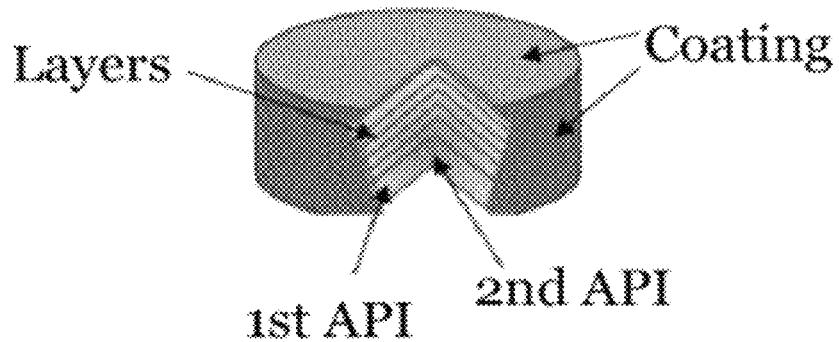

The design of DDS in FIG. 8L has two different APIs, with the second API being provided at a central part of the tablet, and the first API is provided around the second API. At an interface region between both APIs, there is an overlap of the APIs, such that in this interface region, both APIs are arranged. Thereby, a smooth crossover is achieved. Furthermore, layers are provided, extending through the system, which may be hydrophobic layers.

Figure 8M:
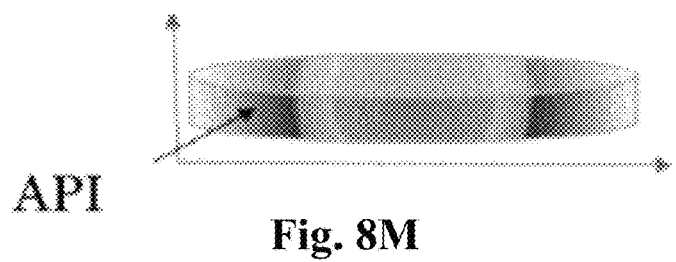

The design of DDS in FIG. 8M does not have a coating. An API is inhomogeneously arranged in the tablet, such that areas or regions with different concentrations of the API are formed.

FIG. 9 illustrates a further design option for a drug delivery system according to the present invention. The system is provided in a spherical shape, and has a hydrophobic coating. The coating comprises hydrophilic pores with sizes in the range of 1 μm to 500 μm. Inside the drug delivery system, there is provided a base paste and three different active pharmaceutical ingredients, API A, API B, and API C. The API C is provided at a central part of the drug delivery system with a peripheral pattern. The other two APIs A and B surround API C. Thereby, API B is provided as a hollow sphere, with a homogeneous distribution of the API. Furthermore, API A is inhomogeneously distributed, surrounding the API C. Thereby, the concentration of API A diminishes towards an edge of the illustrated drug delivery system.

FIG. 10 illustrates a cross-section of a drug delivery system according to the present invention. As can be depicted, the surface of the drug delivery system is structured, as six protrusions and respective recesses in between are formed on one side thereof. By increasing the surface in this manner, the dissolution of the drug delivery system and thus the release of the API can be enhanced. The person skilled in the art understands that the entire surface of the drug delivery system, or only one or several parts thereof may be structured.

Therefore, the person skilled in the art understands that with the drug delivery system produced according to the present invention, a particular inhomogeneous distribution of one or more APIs within the drug delivery system can be arranged in order to provide a desire to release API(s). The person skilled in the art understands that a prompt release or a delayed release of an API can be obtained. Furthermore, it is possible to release a particular single API at different dosages over a prolonged period of time, for example intermittently, thereby obtaining a release of the API in phases.

Furthermore, it is possible to obtain a release of different APIs in distinct phases with a single, novel drug delivery system. For example, it is possible to design the drug delivery system such that a first API is released before a second API is released. Examples for such drug delivery systems integrating two or potentially more APIs include gastroprotective agents such as proton pump inhibitors or antihistamines and non-steroidal anti-inflammatory substances such as ibuprofen or diclofenac. Another example would be the combination of antiemetics (e.g. ondansetron, domperidon) and analgesics, especially those acting on structures of the central nervous system (e.g., tramadolhydrochloride). Another example would be the combination of Carbidopa and Levodopa, thus an agent that prevents the degradation of the pharmaceutically active ingredient. The person skilled in the art understands that the release of these two APIs may provide particular synergetic effects. Furthermore, controlled release could mean mimicry of physiology, e.g. a Cortisone therapy whereas the drug delivery system is administered at 10:00 μm, preferably releasing the steroid 6 hours later. As the steroid is desirably administered at 4:00 am, it is possible to administer the steroid with the drug delivery system according to the present invention, which can be designed such that it is ingested in the previous evening, but the respective API is released at the desired time during the night. Similarly, with the drug delivery system according to the present invention, it is possible to ensure a proper administration of antibiotics in phases, for example, over a prolonged period of time (e.g. over days). Thus, the negative effects of patients disregarding the prescribed administration routine can be reduced.

The person skilled in the art further understands that the usage of the screen-printing technique allows for the production of such elaborate drug delivery systems with high quality, and at great quantities. Thereby, the drug delivery system can be produced in a mass production context.

The design options resulting from the concept of producing an inhomogeneous arrangement of one or more APIs in a drug delivery system are numerous. The person skilled in the art understands that the above examples can be combined to obtain further elaborate designs with release profiles optimized to the particular application or therapy.

The invention claimed is:

1. A method for producing a drug delivery system, the method comprising:
   screen-printing a base paste;
   curing the base paste;
   screen-printing a first paste separate to the base paste;
   curing the first paste;
   wherein the first paste comprises a therapeutically effective amount of a first active pharmaceutical ingredient, API;
   wherein the base paste and the first paste are soluble in body fluids such that the resulting drug delivery system is soluble in body fluids;
   wherein the pastes are screen-printed such that in the resulting drug delivery system the first paste is inhomogeneously arranged in the base paste;
   wherein the pastes are screen-printed such that the base paste is provided as a three-dimensional body and the separate first paste is inhomogeneously arranged throughout the base paste along the three dimensions;
   wherein the pastes are screen-printed such that in the resulting drug delivery system the concentration of the first API varies throughout the drug delivery system;
   wherein a transition from an area in the drug delivery system with a high API concentration to an area in the drug delivery system with a low API concentration is smooth;
   wherein the concentration profile of the first API is such that upon application of the drug delivery system the release of the first API occurs at a varying rate; and
   wherein the first API is a CNS agent.

2. The method of claim 1, wherein the drug delivery system is produced in a layer-by-layer fashion.

3. The method of claim 1, wherein the base paste and the first paste are screen-printed such that a resulting planar layer of the drug delivery system comprises both the base paste and the first paste.

4. The method of claim 3, wherein the planar layer of the drug delivery system is produced by:
   screen-printing and curing the base paste to partially form the planar layer,
   screen-printing and curing the first paste separate to the base paste to partially form the planar layer.

5. The method of claim 4, wherein after finishing the production of the planar layer to produce a finished planar layer, a further planar layer is produced on top of the finished planar layer.

6. The method of claim 1, wherein the base paste is screen-printed at a screen-printer, and wherein the first paste is screen-printed using a separate screen-printer.

7. The method of claim 1, wherein the base paste and the first paste are cured with a shared curing device.

8. The method of claim 1, wherein the pastes are screen-printed such that in the resulting drug delivery system the concentration of the first API is highest at a center, at an edge or at an intermediate region of the drug delivery system.

9. The method of claim 1, wherein the pastes are screen-printed such that in the resulting drug delivery system a gradient of the concentration of the first API increases towards or increases away from a center of the drug delivery system.

10. The method of claim 1, wherein the pastes are screen-printed such that in the resulting drug delivery system a concentration profile of the first API throughout the drug delivery system comprises a smooth transition to an area of increased concentration.

11. The method of claim 1, wherein the pastes are screen-printed such that in the resulting drug delivery system the concentration profile of the first API throughout the drug delivery system comprises more than one area of increased concentration.

12. The method of claim 1, wherein the pastes are screen-printed such that in the resulting drug delivery system the variation of the concentration of the first API throughout the drug delivery system is at least 5%.

13. The method of claim 1, wherein the pastes are screen-printed such that in the resulting drug delivery system the variation of the concentration of the first API throughout the drug delivery system is at most approximately 100%.

14. The method of claim 1, wherein the pastes are screen-printed such that in the resulting drug delivery system the concentration profile of the first API is such that upon application of the drug delivery system, the first API is released from the drug delivery system at a predetermined release profile, which comprises a section with a release at a constant rate.

15. The method of claim 1, wherein the pastes are screen-printed such that in the resulting drug delivery system the concentration profile of the first API is such that upon application of the drug delivery system, the first API is released at two or more dosages, wherein release of the first API at one of the dosages starts 1 second to 10 days.

16. The method of claim 1, wherein the pastes are screen-printed such that the base paste envelops the resulting drug delivery system and the first paste is not arranged at an outer face of the resulting drug delivery system.

17. The method of claim 1, further comprising the steps of:
   screen-printing a second paste separate to the base paste and the first paste;
   curing the second paste;
   wherein the second paste comprises a therapeutically effective amount of a second API.

18. The method of claim 17, wherein the pastes are screen-printed such that a resulting planar layer of the drug delivery system comprises the base paste and the first paste and the second paste.

19. The method of claim 18, wherein the planar layer of the drug delivery system is produced by:
   screen-printing and curing the base paste to partially form the planar layer,
   screen-printing and curing the first paste separate to the base paste to partially form the planar layer, and
   screen-printing and curing the second paste separate from the base paste and the first paste to partially form the planar layer.

20. The method of claim 17, wherein the second paste is soluble in body fluids.

21. The method of claim 17, wherein the pastes are screen-printed such that in the resulting drug delivery system the second paste is inhomogeneously arranged in the base paste.

22. The method of claim 17, wherein the pastes are screen-printed such that in the resulting drug delivery system the concentration profile of the first API throughout the drug delivery system is different than the concentration profile of the second API throughout the drug delivery system.

23. The method of claim 17, wherein the pastes are screen-printed such that upon application of the resulting drug delivery system, release of the first API starts before release of the second API, wherein the release of the first API starts 1 second to 10 days.

24. The method of claim 17, wherein the pastes are screen-printed such that upon application of the resulting drug delivery system, a release profile of the first API differs from a release profile of the second API.

25. The method of claim 1, wherein the first paste is screen-printed to form a geometrical shape, the shape selected from
   a tube,
   a spot,
   an oval,
   a plate, and
   a polygon.

26. The method of claim 1, wherein the resulting drug delivery system is in the form of
   a tablet,
   a capsule,
   a disk,
   a film,
   an implant,
   a subdermal implant,
   a patch,
   pellets, or
   granules.

27. The method of claim 1, wherein the first API is selected from a list comprising narcotics and narcotic antagonists, sedative hypnotics, analeptics, antiparkinson agents, neuroleptic agents.

28. The method of claim 1, wherein the first API is selected from a list comprising Pregabalin, Lurasidon, Fentanyl, Varenicline, Memantine, Zolmitriptan, Lacosamid, Desvenlafaxin, Aripiprazole, Levodopa.

29. The method of claim 1, wherein the base paste and the first paste are soluble in body fluids such that the resulting drug delivery system is soluble in body fluids.

30. The method of claim 1, wherein the pastes are screen-printed such that in the resulting drug delivery system the first paste is inhomogeneously arranged in the base paste.

31. The method of claim 1, wherein the pastes are screen-printed such that the base paste is provided as a three-dimensional body and the separate first paste is inhomogeneously arranged throughout the base paste along the three dimensions.

32. The method of claim 1, wherein the pastes are screen-printed such that in the result drug delivery system the concentration of the first API varies throughout the drug delivery system.

33. The method of claim 1, wherein the concentration profile of the first API is such that upon application of the drug delivery system the release of the first API occurs at a varying rate.

* * * * *